United States Patent
Kaplan et al.

[11] Patent Number: 5,147,400
[45] Date of Patent: Sep. 15, 1992

[54] CONNECTIVE TISSUE PROSTHESIS

[75] Inventors: Donald S. Kaplan, Weston; John Kennedy, Stratford; Ross R. Muth, Brookfield, all of Conn.

[73] Assignee: United States Surgical Corporation, Norwalk, Conn.

[21] Appl. No.: 581,462

[22] Filed: Sep. 12, 1990

Related U.S. Application Data

[63] Continuation-in-part of Ser. No. 349,648, May 10, 1989, Pat. No. 4,990,158.

[51] Int. Cl.$^5$ ............................................. A61F 2/08
[52] U.S. Cl. ......................................... 623/13; 623/1; 623/11; 623/66
[58] Field of Search .................. 623/1, 13, 11

[56] References Cited

U.S. PATENT DOCUMENTS 3,463,158  8/1969  Schmitt et al. .
3,537,280  11/1970  Garrou et al. .
3,688,317  9/1972  Kurtz .
3,805,300  4/1974  Tascon-Alonso et al. .
3,878,565  4/1975  Sauvage .
4,047,252  9/1977  Liebig et al. .
4,187,558  2/1980  Dahlen et al. .
4,193,138  3/1980  Okita .
4,208,745  6/1980  Okita .
4,229,838  10/1980  Mano .
4,286,341  9/1981  Greer et al. .
4,301,551  11/1981  Dore et al. .
4,340,091  7/1982  Skelton et al. .
4,350,731  9/1982  Siracusano .
4,378,017  3/1983  Kosugi et al. .
4,467,595  8/1984  Kramers .
4,474,851  10/1984  Urry .
4,483,023  11/1984  Hoffman, Jr. et al. .
4,517,687  5/1985  Liebig et al. .
4,530,113  7/1985  Matterson .
4,584,722  4/1986  Levy et al. .
4,610,688  9/1986  Silvestrini et al. .
4,621,638  11/1986  Silvestrini .
4,624,256  11/1986  Messier et al. .
4,642,119  2/1987  Shah .
4,663,221  5/1987  Makimura et al. .
4,668,233  5/1987  Seedhom et al. .
4,693,720  9/1987  Scharnberg et al. .
4,713,070  12/1987  Mano .
4,713,075  12/1987  Kurland .
4,718,907  1/1988  Karwoski et al. .
4,775,380  10/1988  Seedhom et al. .
4,788,979  12/1988  Jarrett et al. .
4,816,028  3/1989  Kapadia et al. .
4,816,339  3/1989  Tu et al. .
4,822,361  4/1989  Okita et al. .
4,871,365  10/1989  Dumican .
4,894,063  1/1990  Nashef .
4,942,875  7/1990  Hlavacek et al. .
4,990,158  2/1991  Kaplan et al. ................. 623/1

FOREIGN PATENT DOCUMENTS 0169045  1/1986  European Pat. Off. .
0202444  11/1986  European Pat. Off. .
0239775  10/1987  European Pat. Off. .
0241252  10/1987  European Pat. Off. .
0334046  9/1989  European Pat. Off. .
WO8400302  2/1984  PCT Int'l Appl. .
8901320  2/1989  World Int. Prop. O. ........ 623/13

OTHER PUBLICATIONS

Am. J. Sports Med. 7,1: 18-22 (1979).
Am. J. Sports Med. 8,6: 395-401 (1980).
Am. J. Sports Med. 10,5: 259-265 (1982).
Orthrop Trans 7: 174-175 (1983).
Feagin, Jr., "The Crucial Ligaments", -Churchill Livingstone, New York (1988), pp. 540-544.

*Primary Examiner*—David Isabella
*Assistant Examiner*—Debra S. Brittingham
*Attorney, Agent, or Firm*—Thomas R. Bremer; Peter G. Dilworth; Rocco S. Barrese

[57] ABSTRACT

A semi-bioabsorbable connective tissue prosthesis, e.g., a replacement for the human anterior cruciate ligament, is provided whose stress-strain characteristics closely match those of the natural tissue.

58 Claims, 5 Drawing Sheets

FIG. 6
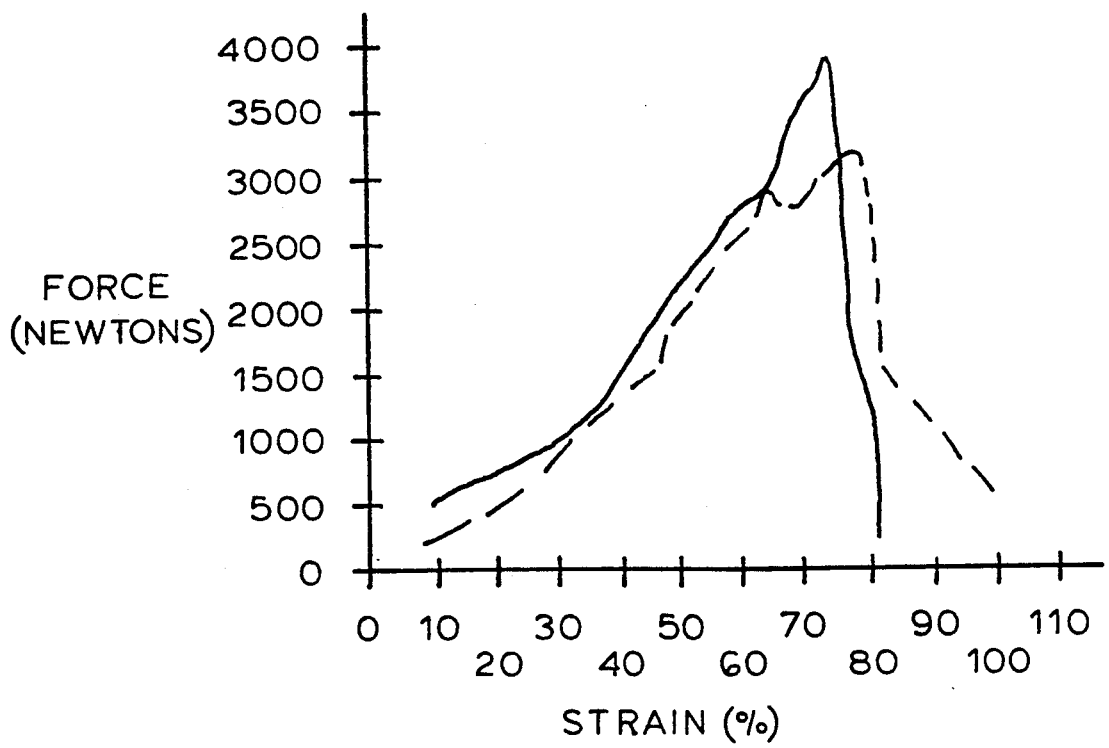
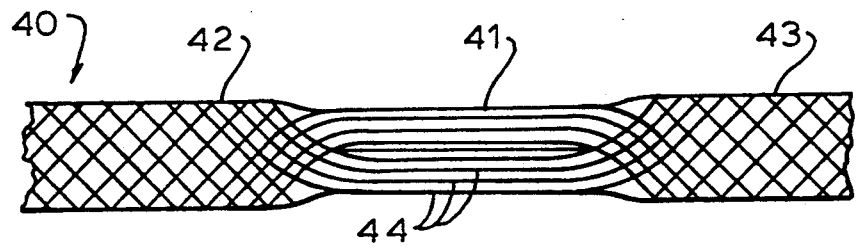
FIG. 7
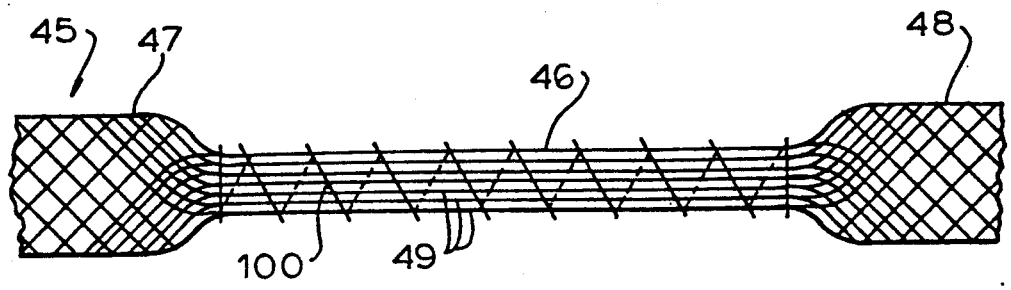
FIG. 8

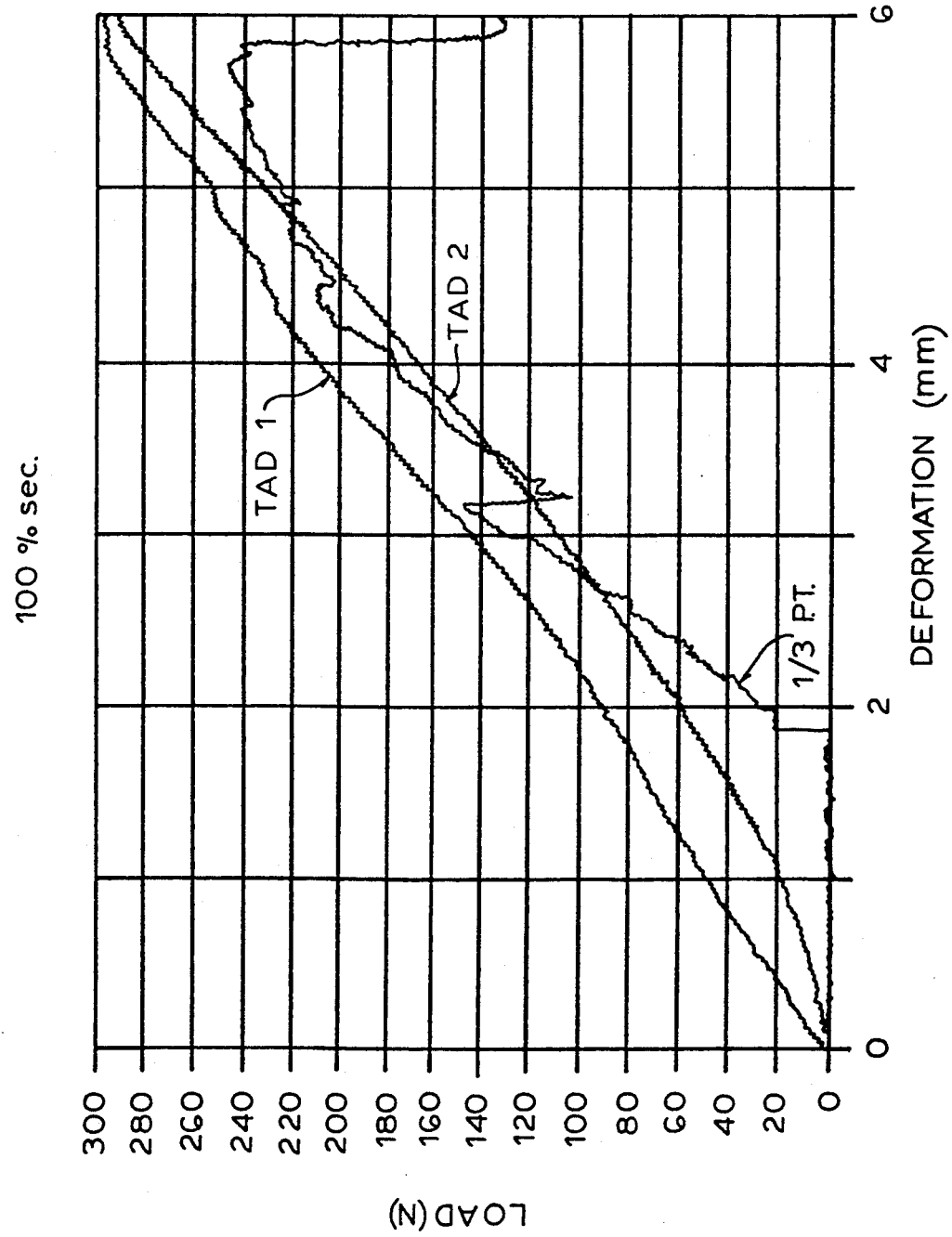

CONNECTIVE TISSUE PROSTHESIS

CROSS REFERENCE TO RELATED APPLICATION

The application is a continuation-in-part of commonly assigned, co-pending U.S. patent application Ser. No. 349,648, filed May 10, 1989, now U.S. Pat. No. 4,990,158.

BACKGROUND OF THE INVENTION

This invention relates to a connective tissue prosthesis and, in particular, to a biocompatible ligament or tendon prosthesis which closely approximates the biomechanical characteristics of the natural tissue to be replaced or augmented.

Numerous connective tissue materials and constructions have been proposed for use as temporary or permanent grafts in ligament and tendon repair. Feagin, Jr., Ed., *The Crucial Ligaments/Diagnosis and Treatment of Ligamentous Injuries About the Knee* (Churchhill Livingstone, N.Y., 1988) describes a number of partially bioabsorbable materials which have been investigated for use as ligament grafts. In Chapter 33 of this publication (Rodkey, "Laboratory Studies of Biodegradable materials for Cruciate Ligament Reconstruction"), it is reported that while a 100 percent biodegradable ligament fabricated from polyglycolic acid (PGA) was found to be safe, strong, well-tolerated and provided stability for the repaired anterior cruciate ligament in dogs, its complete resorption within five weeks makes it unsuitable for use in prostheses intended for humans since a human ligament prosthesis must provide support over a much longer period of time. It is further reported that a study in dogs of the intraarticular use of a partially biodegradable ligament prosthesis possessing a Dacron (i.e., DuPont's polyethylene terephthalate (PET)) and PGA core and a separate outer sleeve woven from PGA and Dacron of a different percentage of composition gave disappointing results.

U.S. Pat. Nos. 4,792,336 and 4,942,875 describe a surgical device for repairing or augmenting connective tissue and comprising a plurality of fibers, in which the majority of the fibers are in a direction essentially parallel to the length of the device and can be either 100 percent bioabsorbable or can contain a nonabsorbable component. Additionally, sleeve yarns consisting completely of absorbable material wrap around these axial or warp yarns.

Biomedical Business International Report No. 7041 (Second Revision, May 1986), "Orthopaedic and Diagnostic Devices", pages 5—5 to 5-12, identifies a variety of materials which have been used in the fabrication of prosthetic ligaments including carbon fiber, expanded Teflon (i.e., DuPont's polytetrafluoroethylene), a combination of silicone and PET, polypropylene, polyethylene, nickel-chromium alloy fibers individually enclosed in synthetic textile or natural silk, carbon material coated with gelatin, polyester combined with PET fibers, bovine tissues, and others.

Other disclosures of ligament and tendon repair devices are provided, inter alia, in U.S. Pat. Nos. 3,805,300; 4,187,558; 4,301,551; 4,483,023; 4,584,722; 4,610,688; 4,668,233; 4,775,380; 4,788,979; and PCT Patent Publication No. WO 89/01320.

Chapter 33 (page 540) of the Feagin, Jr. publication referred to above identifies the characteristics of an ideal ligament prosthesis as follows:

(1) it must be durable with adequate strength to withstand the extreme forces placed upon it, yet compliant enough to allow for repetitive motion without failure or excessive creep elongation;

(2) it must be tolerated by the host with no antigenic or carcinogenic reaction;

(3) if partially or completely biodegradable, the size of the individual fibers and the construction pattern must be appropriate to support and allow eventual reconstitution of the repaired structure with ingrowth of fibrous tissue that matures to normal or near normal collagen;

(4) it must tolerate sterilization and storage; and (5) it should be easily implanted using surgical and potentially arthroscopic techniques.

The existence of so many different types of materials and devices for use in connective tissue repair, some of which have been identified above, bears testimony to the difficulty of meeting some, much less all, of the foregoing characteristics in a single prosthetic device.

SUMMARY OF THE INVENTION

It is a principal object of the invention to provide a semi-bioabsorbable or fully bioabsorbable connective tissue prosthesis, e.g., a ligament or tendon repair device, which exhibits the stress-strain properties of the natural tissue to be replaced or augmented.

It is a specific object of the invention to provide the foregoing connective tissue prosthesis as a structure formed from a composite yarn comprising a non-bioabsorbable core yarn surrounded by a bioabsorbable or semi-bioabsorbable cover or sheath yarn.

It is a further specific object of the invention to provide a connective tissue prosthesis formed from a composite yarn wherein an elastic core yarn is wrapped with a relatively inelastic, bioabsorbable or semi-bioabsorbable sheath yarn, so as to exhibit the stress-strain properties of natural tissue.

It is another specific object of the invention to provide a prosthetic replacement for a human anterior cruciate ligament which is based on the aforesaid structure, in particular, one fabricated from a yarn whose sheath yarn component is derived from a glycolide-lactide copolymer.

In keeping with these and other objects of the invention, there is provided a connective tissue prosthesis comprising:

(a) a core made up of a first biocompatible composite yarn extending in the lengthwise direction; and (b) a sheath surrounding the core and fabricated from a second biocompatible yarn, wherein the first composite yarn in the core (a) comprises a biocompatible, non-bioabsorbable core yarn component surrounded by a biocompatible, bioabsorbable or semi-bioabsorbable sheath yarn component.

The second biocompatible yarn forming the sheath (b) may be the same as, or different from, the first composite yarn which forms the core (a). More specifically, the second biocompatible yarn may also comprise a biocompatible, non-bioabsorbable core yarn component surrounded by a biocompatible, bioabsorbable or semibioabsorbable sheath yarn component.

Also in keeping with the above and other objects of the invention, a connective tissue prosthesis is provided which comprises a tubular component fabricated from composite yarn, the yarn comprising a biocompatible, nonbioabsorbable core yarn component surrounded by a biocompatible, bioabsorbable or semi-bioabsorbable sheath yarn component.

The foregoing connective tissue prostheses meet the Feagin, Jr. criteria, identified sucra, to a surprising degree. Due to elasticity of the composite yarn core component and relative inelasticity of the composite yarn sheath component, the stress-strain characteristics of the connective tissue prostheses closely match those of the natural tissue which they replace and their resorption properties can be calibrated to maintain the functionality of the prostheses throughout the entire period of the tissue regeneration process. The prostheses of this invention are readily sterilizable, possess good storage stability when suitably protected from hydrolytic forces, and can be installed at a ligament, tendon, vascular, or tracheal repair site employing known surgical reconstruction techniques.

BRIEF DESCRIPTION OF THE DRAWINGS

FIG. 6 is a plot of experimental data showing the stress-strain characteristics of the prosthesis of FIG. 5 compared with the stress-strain characteristics of a natural ligament as reported in the literature;

FIG. 7 represents a section of a tubular ligament prosthesis manufactured from the composite yarn of the present invention and having an unbraided center section;

FIG. 8 represents a section of a tubular ligament prosthesis similar to FIG. 7 and additionally having the unbraided center section helically wrapped with a yarn;

FIG. 12 is a plot of experimental data showing the stress-strain characteristics of the prosthesis of FIG. 7 compared with a canine patellar tendon.

DESCRIPTION OF THE PREFERRED EMBODIMENTS

Figure 1:
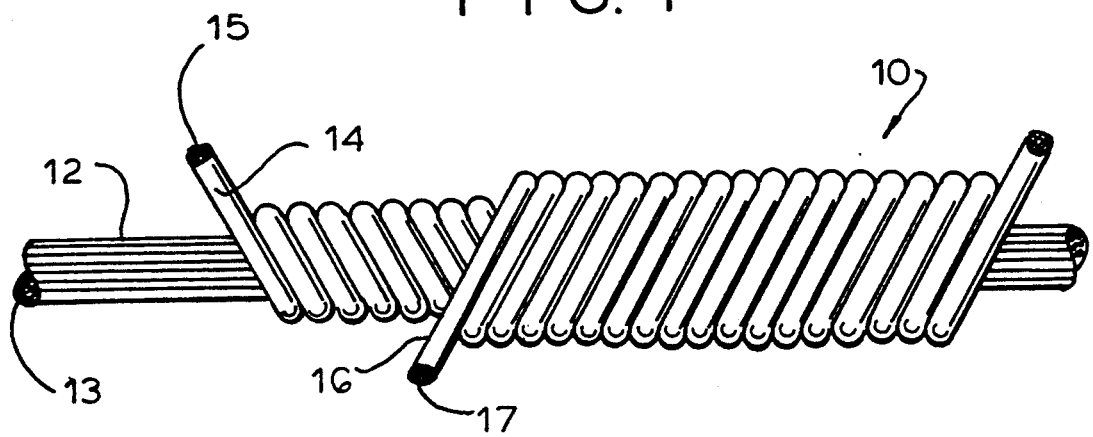
FIGS. 1 and 2 are enlarged isometric views of composite yarns which are utilized in the construction of the connective tissue prosthesis herein.

As shown in FIG. 1, composite yarn 10 comprises a core yarn component 12 made up of a multiplicity of individual biocompatible, essentially non-bioabsorbable and preferably elastic filaments 13, advantageously provided with a slight to moderate twist, and a sheath yarn component 14 made up of a multiplicity of individual biocompatible, bioabsorbable or semi-bioabsorbable and preferably relatively inelastic filaments 15 wound in a first direction around the core and an external multifilamentous sheath yarn component 16, also made up of individual biocompatible, bioabsorbable or semi-bioabsorbable and preferably relatively inelastic filaments 17, wound in a second and opposite direction around sheath yarn component 14. For example, multifilamentous sheath yarn component 16 may comprise both absorbable and non-absorbable filaments 17. Generally, the filaments 13 of core yarn component 12 are substantially parallel.

Non-bioabsorbable core yarn component 12 functions to impart elasticity to composite yarn 10 and acts as a scaffolding during and after absorption of the bioabsorbable sheath. Bioabsorbable sheath yarn components 14 and 16 function to provide the composite yarn with relative inelasticity, tensile strength, and absorption characteristics which allow for desirable tissue ingrowth and incorporation of the composite yarn into the body structure. Sheath yarn components 14 and 16 each have a lengthwise axis which is non-perpendicular to the lengthwise axis of core component 12. While core yarn component 12 can be wrapped with a single layer of sheath yarn component, the illustrated arrangement of two layers of sheath yarn components 14 and 16 is generally preferred as this construction helps to give composite yarn 10 a balanced structure which resists crimping or kinking when used in the manufacture of a prosthesis such as shown in FIGS. 5 and 7-11.

Where, as shown in the embodiment of FIG. 1, at least two sheath yarn components are employed in the construction of the composite yarn, the composition, number and denier of the individual filaments, and braiding (if any) of these yarn components as well as their relative rates of bioabsorption can differ. For example, non-absorbable filaments may be combined with absorbable filaments to provide one or more semiabsorbable sheath yarn components. This capability for differential absorption can be advantageously exploited in a connective tissue prosthetic device in which the outermost sheath yarn component is absorbed by the body at a faster rate than the underlying sheath yarn component, or vice versa. thus resulting in a staged absorption of the sheath components of the composite yarn.

Core yarn component 12 must be essentially non-bioabsorbable, i.e., it must resist degradation when, as part of the connective tissue prosthesis of this invention, it is implanted in a body. The term "non-bioabsorbable" as used herein applies to materials which permanently remain within the body or at least remain in the body for a relatively long period of time, e.g., at least about two years. It is preferred to employ a core yarn material which is also elastic, i.e, a polymeric material which in filamentous form exhibits a relatively high degree of reversible extensibility, e.g., an elongation at break of at least about 30 percent, preferably at least about 40 percent and more preferably at least about 50 percent. Fiber-forming polymers which are both non-bioabsorbable and elastic, and as such preferred for use as the core yarn component herein, include fiber-forming polyolefins such as polyethylene homopolymers, polypropylene homopolymers, ethylene propylene copolymers, ethylene propylene terpolymers, etc., fluorinated hydrocarbons, fluorosilicones, isobutylenes, isoprenes, polyacrylates, polybutadienes, polyurethanes, polyether-polyester copolymers, and the like. Hytrel (DuPont), a family of copolyester elastomers based on (soft) polyether segments and (hard) polyester segments, and spandex, an elastomeric segmented polyurethane, provide especially good results.

Hytrel is manufactured in various commercial grades by DuPont, such as Hytrel 4056, 5526, 5556 and 7246. Hytrel 5556 is especially suitable as the core component 12 of the composite yarn 10 when used to form a vascular graft, while Hytrel 7246 is well-suited for the core component 12 of the composite yarn 10 when used to form a ligament prosthesis or tendon augmentation device.

Several properties of the various Hytrel grades are presented in the table below:

drophilic coatings which are suitable for this purpose include polymeric materials such as the sparingly cross-linked poly(hydroxyethyl methacrylate) hydrogels disclosed in U.S. Pat. Nos. 2,976,576 and 3,220,960; hydrogels based on cross-linked polymers of n-vinyl lactams and alkyl acrylates as disclosed in U.S. Pat. No. 3,532,679; graft copolymers of hydroxyalkyl methacrylate and polyvinylpyrrolidone disclosed in U.S. Pat. No. 3,621,079, and many others.

Fiber-forming materials which are relatively inelastic are suitable for providing the sheath yarn component of composite yarn 10 provided such materials are fairly

|  | Hytrel Grade No. (Injection Molded at 23° C. for Testing) | | | |
| --- | --- | --- | --- | --- |
|  | 4056 | 5526 | 5556 | 7246 |
| Hardness in durometer points (ASTM Test No. D2240) | 40 | 55 | 55 | 72 |
| Flexural Modulus (ASTM Test No. D790) | | | | |
| at −40° C. in MPa | 155 | 930 | 930 | 2,410 |
| at −40° F. in psi | 22,500 | 135,000 | 135,000 | 350,000 |
| at 23° C. in MPa | 55 | 207 | 207 | 518 |
| at 73° F. in psi | 8,000 | 30,000 | 30,000 | 75,000 |
| at 100° C. in MPa | 27 | 110 | 110 | 207 |
| at 212° F. in psi | 3,900 | 16,000 | 16,000 | 30,000 |
| ASTM Test No. D638 | | | | |
| $^{(i)}$Tensile Strength at Break, | | | | |
| MPa | 28.0 | 40.0 | 40.0 | 45.8 |
| psi | 4050 | 5800 | 5800 | 6650 |
| $^{(i)}$Elongation at Break, % | 550 | 500 | 500 | 350 |
| $^{(ii)}$Tensile Stress at 5% Strain, | | | | |
| MPa | 2.4 | 6.9 | 6.9 | 14.0 |
| psi | 350 | 1,000 | 1,000 | 2,025 |
| $^{(ii)}$Tensile Stress at 10% Strain, | | | | |
| Mpa | 3.6 | 10.3 | 10.3 | 20.0 |
| psi | 525 | 1,500 | 1,500 | 2,900 |
| Izod Impact (Notched) (ASTM Test No. D256, Method A) | | | | |
| at −40° C. in J/cm | No Break | No Break | No Break | 0.4 |
| at −40° F. in ft-lbf/in | No Break | No Break | No Break | 0.8 |
| at 23° C. in J/cm | No Break | No Break | No Break | 2.1 |
| at 73° F. in ft-lbf/in. | No Break | No Break | No Break | 3.9 |
| Resistance to Flex Cut Growth, Ross (Pierced), in Cycles to 100% cut growth (ASTM Test No. D1052) | $>1 \times 10^6$ | $>5 \times 10^5$ | $>5 \times 10^5$ | — |
| $^{(iii)}$Initial Tear Resistance, Die C (ASTM Test No. D1004), | | | | |
| in kN/m | 101 | 158 | 158 | 200 |
| in lbf/in. | 580 | 900 | 900 | 1,146 |
| Melt Flow Rate in g/10 min. (ASTM Test No. D1238) | 5.3 | 18 | 7.0 | 12.5 |
| Test Conditions: Temperature, °C./Load, Kg | 190/2.16 | 220/2.16 | 220/2.16 | 240/2.16 |
| $^{(iv)}$Melting Point (ASTM Test No. D3418) | | | | |
| in °C. | 148 | 202 | 202 | 219 |
| in °F. | 298 | 396 | 396 | 426 |
| Vicat Softening Point (ASTM Test No. D1525) | | | | |
| in °C. | 108 | 180 | 180 | 207 |
| in °F. | 226 | 356 | 356 | 405 |
| Specific Gravity (ASTM Test No. D792) | 1.16 | 1.20 | 1.20 | 1.25 |
| Water Absorption, 24 hr. in % (ASTM Test No. D570) | 0.6 | 0.5 | 0.5 | 0.3 |

$^{(i)}$head speed 50 mm/min. or 2 in/min.
$^{(ii)}$head speed 25 mm/min. or 1 in/min.
$^{(iii)}$specimens 1.9 mm or 0.075 in. thick.
$^{(iv)}$differential scanning calorimeter (DSC), peak of endotherm Corresponding properties of other grades of Hytrel are available from DuPont.

If desired, the core yarn component can be provided with a nonabsorbable hydrophilic coating to improve its wettability by body fluids, e.g., synovial fluid. Hyrapidly bioabsorbed by the body, e.g., exhibiting a loss of tensile strength in from about 2 to about 26 weeks and total absorption within from about two to about fifty two weeks. It is to be understood, however, that the expression "relatively inelastic" does not preclude the presence of some minor degree of elasticity in the sheath yarn component, merely that it excludes a degree of elastic behavior as described in connection with the preferred type of core yarn component.

The sheath yarn component can be woven, braided or knitted in whole or in part and will ordinarily possess a relatively high tensile strength, e.g., a straight tensile strength of at least about 30,000 p.s.i., preferably at least about 60,000 p.s.i. and more preferably at least about 90,000 p.s.i.

Bioabsorbable, relatively inelastic fiber-forming polymers and polymer blends from which the sheath yarn component herein can be formed include those derived at least in part from such monomers as glycolic acid, glycolide, lactic acid, lactide, p-dioxanone, trimethylene carbonate, e-caprolactone, hydroxycaproic acid, etc., and various combinations of these and related monomers as disclosed, e.g., in U.S. Pat. Nos. 2,668,162; 2,703,316; 2,758,987; 3,225,766; 3,297,033; 3,422,181; 3,531,561; 3,565,077; 3,565,869; 3,620,218; 3,626,948; 3,636,956; 3,736,646; 3,772,420; 3,773,919; 3,792,010; 3,797,499; 3,839,297; 3,867,190; 3,878,284; 3,982,543; 4,047,533; 4,052,988; 4,060,089; 4,137,921; 4,157,437; 4,234,775; 4,237,920; 4,300,565; 4,429,080; 4,441,496; 4,523,591; 4,546,152; 4,559,945; 4,643,191; 4,646,741; 4,653,497; and, 4,741,337; U.K. Patent No. 779,291; D. K. Gilding et al., "Biodegradable polymers for use in surgery—polyglycolide/poly(lactic acid) homo- and copolymers: 1", *Polymer*, Volume 20, pages 1459–1464 (1979), and D. F. Williams (ed.), *Biocompatibility of Clinical Implant Materials*, Vol. II, ch. 9: "Biodegradable Polymers" (1981).

Sheath yarn components manufactured from polymers of high lactide or glycolide content, e.g., those in which at least about 75 percent of the monomeric units are derived from either glycolide or lactide, are preferred for the construction of the composite yarn of this invention. Polymers of high glycolide content tend to be absorbed more quickly than those possessing a high lactide content. Accordingly, the glycolide-based polymers may be preferred for the manufacture of a sheath yarn component providing the outermost sheath yarn(s) in a multiple sheath yarn component construction, the underlying internal sheath yarn(s) being manufactured from the more slowly absorbable lactide-based polymers. An especially preferred lactide-glycolide copolymer for forming the sheath yarn component of the composite yarn contains from about 70 to about 90, and preferably from about 75 to about 85 mole percent lactide monomer with the balance being provided by the glycolide monomer. Thus, for example, a sheath yarn component formed from a lactide-glycolide copolymer based on 80 mole percent lactide-20 mole percent glycolide is especially advantageous for constructing the composite yarn, and ultimately, the connective tissue prosthesis, of the present invention. The sheath yarn component, which is preferably braided around the core yarn component, may comprise a plurality of bioabsorbable fibers in turn comprising at least two different chemical compositions.

The deniers of core yarn component 12 and sheath yarn components 14 and 16 are not especially critical and those of commercially available yarns such as Vicryl (a glycolide/lactide copolymer suture available from Ethicon) and Dexon (a polyglycolide suture available from American Cyanamid) are suitably employed.

Preferably, the deniers are selected so as to provide a composite yarn having an overall denier of from about 40 to about 1200 and preferably from about 80 to about 500, the overall denier of the core and/or sheath yarn components being from about 20 to about 600 and preferably from about 40 to about 300. The deniers of individual filaments in the core and sheath yarn components of multifilamentous construction can vary widely, e.g., from about 0.2 to about 6.0 and preferably from about 0.4 to about 3.0. The base weight for a desired composite yarn will determine the size and weight of the component elements of the yarn. Composite yarn 10 possesses sufficient core material to impart, inter alia, a desired resiliency and sufficient sheath material to provide, inter alia. a desired tensile strength for a particular connective tissue prosthetic application. In general, the core component can represent from about 20 to about 80 percent, and preferably from about 30 to about 70 percent of the total weight of composite yarn 10. Optimum core and sheath component weights will naturally vary depending on the specific application and can be readily determined in a given case based on the desired physical properties of the prosthetic device without undue experimentation.

Methods and apparatus for covering core yarn components with sheath yarn components are well known and need not be described here in detail. In general, the sheath yarn components are wrapped about the core yarn component on a covering machine which includes a hollow spindle with rotating yarn supply bobbins supported thereon. The elastic core yarn component is fed through the hollow spindle and the elastic sheath yarn components are withdrawn from the alternate direction rotating supply bobbins and wrapped about the core yarn component as it emerges from the hollow spindle. The core yarn component is preferably under a slight tension during the covering procedure and the sheath yarn components are laid down in a side-by-side array. The number of wraps per inch will depend on the denier of the sheath yarn components but should be sufficient to cause the sheath yarn components to lay close to the core yarn component when tension on the latter is relaxed.

As desired, the filaments which comprise a sheath yarn component can be provided with no twist or with varying degrees of twist. Where the yarns are twisted, it can be advantageous to balance or equalize the twist in the final composite yarn structure. Thus, for example, in the embodiment of composite yarn 10 in FIG. 1, if sheath yarn component 14 has a given twist, sheath yarn component 16 should have an equivalent twist. Since sheath yarn components 14 and 16 are laid down in opposite directions, the twist in each of these yarn components will be neutralized in the final structure of the composite yarn. Similarly, sheath yarn components 14 and 16 are advantageously of about equal weight in order to provide further balance in the composite yarn.

Figure 2:
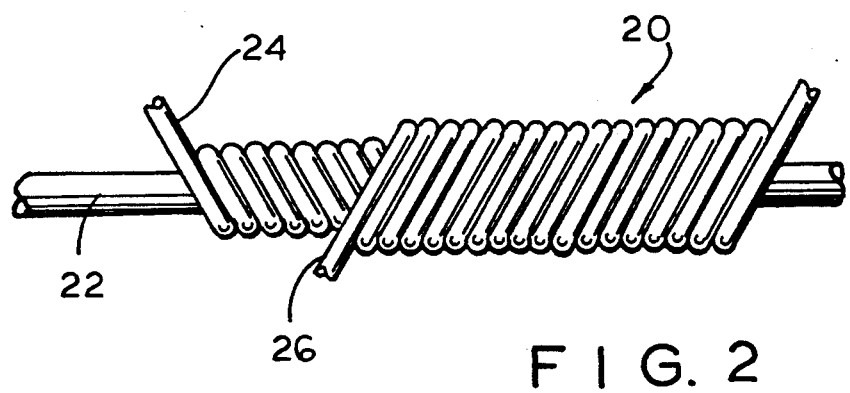

The composite yarn 20 shown in FIG. 2 is similar to that of FIG. 1 except that core yarn component 22 constitutes a monofilament and internal and external sheath yarn components 24 and 26, respectively, each constitutes a monofilament. In all other structural and compositional respects, composite yarn 20 can be like that of composite yarn 10.

Figure 3:
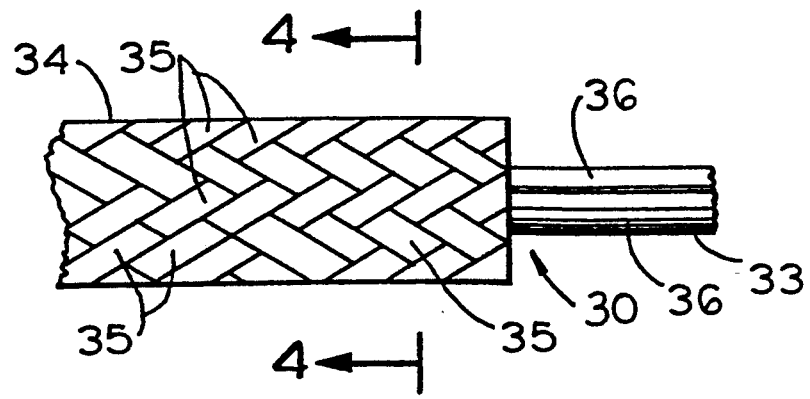
FIG. 3 is an enlarged isometric view of an alternative composite yarn utilized in the construction of the connective tissue prosthesis herein.
Figure 4:
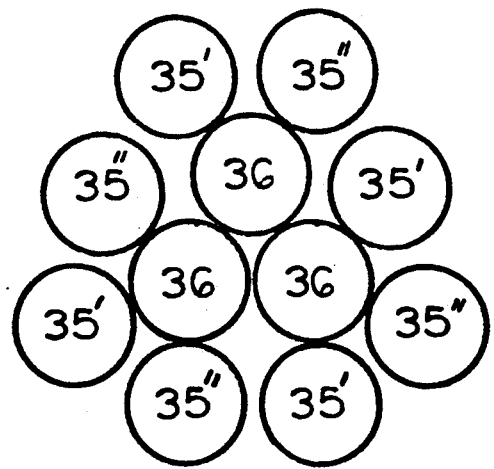
FIG. 4 is a schematic, cross-sectional view along line 4—4 of FIG. 3.

An alternative composite yarn 30 is illustrated in FIGS. 3 and 4. Composite yarn 30 comprises a core yarn component 33 and a braided sheath yarn component 34. As with core yarn components 12 and 22 of FIGS. 1 and 2, core yarn component 33 is made up of one or more biocompatible, essentially non-bioabsorbable and preferably elastic filaments 36 which define the longitudinal axis of composite yarn 30. Braided sheath yarn component 34 comprises individual sheath yarn filaments or sheath yarn filament bundles 35 which traverse core yarn component 33 in a substantially conventional braided configuration to provide core yarn component 33 with a braided tubular external sheath 34. The individual sheath yarn filaments or sheath yarn filament bundles 35 are biocompatible, bioabsorbable or semi-bioabsorbable, and relatively inelastic. In a preferred embodiment of the present invention as illustrated in FIGS. 3 and 4, sheath yarn component 34 comprises sheath yarn filaments of different chemical composition. For example, a portion of the sheath yarn filaments 35', e.g., 30 to 70% by weight, may be formed of a bioabsorbable polymer exhibiting relatively slow bioabsorption, e.g., polylactide or a copolymer comprising a high lactide mole percentage, while the remainder of the sheath yarn filaments 35" may be formed of a second bioabsorbable polymer which exhibits relatively fast bioabsorption, e.g., polyglycolide or a copolymer comprising a high glycolide mole percentage. Sheath yarn component 34 may also be fabricated from individual filaments having more than two different chemical compositions, one or more of which optionally being nonbioabsorbable.

In the embodiment illustrated in FIGS. 3 and 4, core yarn component 33 is preferably manufactured from Hytrel filaments 36 and has a denier of about 270, while sheath yarn component 34, which is braided on an eight carrier braider, has a denier of about 204, for a total denier of this composite yarn 30 of about 474.

Figure 5:
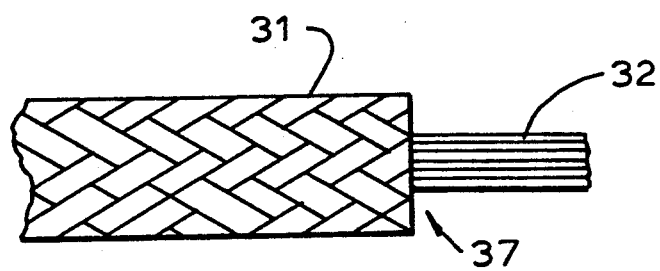
FIG. 5 represents a section of a ligament prosthesis manufactured from the composite yarn of FIG. 1 and suitable for use in the surgical reconstruction of the human anterior cruciate ligament.

FIG. 5 illustrates an anterior cruciate ligament prosthesis 37 manufactured from warp and filling composite yarns 10 of FIG. 1. Prosthesis 37 is constructed by constructing a sheath 31 about core 32 by weaving, braiding or knitting on a known or conventional loom. For example, the sheath may be braided about the core on a braiding machine which includes braider bobbins. Composite yarn forming the sheath may be wound onto an appropriate number of braider bobbins which are then loaded onto a carrier braider with the yarns on the bobbins then being braided and tied to form the sheath. The core (if one is required) can be pulled through the sheath, e.g. manually to form the prosthesis. In other words, the core will be at least partially surrounded by the sheath. Other prostheses illustrated herein can be manufactured in similar fashion. The sheath components of the individual composite yarns from which ligament prosthesis 30 is manufactured will erode over time due to their bioabsorption leaving only the nonabsorbable core component as a permanent or long term scaffold for new ligament tissue growth.

FIGS. 7-11 illustrate examples of other ligament prostheses which can be manufactured from the composite yarn of the present invention, e.g. as illustrated in FIGS. 1-3. More particularly, FIG. 7 illustrates a tubular ligament prosthesis or tendon augmentation device 40 having an unbraided center section 41 bounded by braided sections 42 and 43. The individual composite yarns 44 in the unbraided center section 41 can be drawn in generally parallel relationship, if required. The length of the unbraided center section 41 can vary, e.g., from about one or two inches up to about seven or eight inches. The unbraided center section 41 provides tensile strength and/or tissue ingrowth advantages.

Additionally, a tubular ligament prosthesis or tendon augmentation device 45 as illustrated in FIG. 8 can be manufactured from the composite yarn of the present invention. The prosthesis 45 is similar to the one illustrated in FIG. 7 and comprises an unbraided center section 46 bounded by braided sections 47 and 48. A helical wrap 100 is provided about the unbraided center section 46 to improve handling and manipulation of the unbraided section 46 during implantation, while absorption/degradation of the helical wrap 100 frees the individual yarns 49 of the center unbraided section 46 to provide the appropriate tensile strength and/or tissue ingrowth advantages. In this regard, the yarn forming the helical wrap 100 can be the composite yarn of FIGS. 1-3 or formed of a different kind of material, e.g. completely bioabsorbable or nonbioabsorbable material. The tubular ligament prostheses of FIGS. 7 and 8 are both constructed by braiding the end sections 42, 43 or 47, 48 in a known or conventional loom and, in the case of FIG. 8, additionally wrapping the helical yarn 100 about the center unbraided section 46, also with a known or conventional loom. The prostheses of FIGS. 7 and 8 are especially suitable as replacements for anterior cruciate ligaments.

Figure 9:
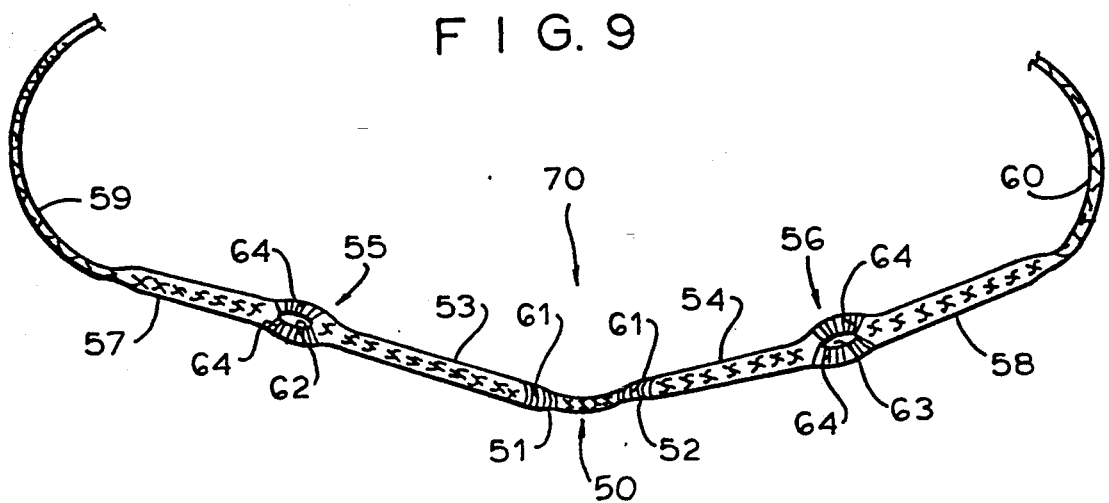
FIG. 9 represents a section of a braided prosthesis manufactured from composite yarn of the present invention and modified in various fashion over the length thereof.

FIG. 9 illustrates a braided prosthesis 70 which can be manufactured from the composite yarns of FIGS. 1-3 and which is also modified along the length thereof. More specifically, the prosthesis of FIG. 9 comprises a center region 50 bordered by first outer regions 51, 52, second outer regions 53, 54, third outer regions 55, 56, fourth outer regions 57, 58, and fifth outer regions 59, 60. The center region 50 comprises a sheath of braided composite yarn, e.g., as illustrated in FIGS. 1-3, about a core (not illustrated) also formed of composite yarn. First outer regions 51, 52 additionally comprise a wrapping 61 about the braided yarn, this wrapping 61 being formed of the same composite yarn as illustrated in FIGS. 1-3 or a different kind of material, e.g. a totally bioabsorbable or nonabsorbable material. This wrapping 61 serves to at least temporarily retain the sheath about the core.

The second outer regions 53, 54 also formed of tubular braided composite yarn as illustrated in FIGS. 1-3 with an appropriate core material (not illustrated) that forms a thicker core than any core present in center section 50 (the center section 50 can be coreless, if required). Third outer regions 55, 56 are divided as illustrated in FIG. 9 to form respective openings 62 and 63. This allows attachment means to be inserted through the respective openings to secure the ligament prosthesis 70 in place. As illustrated in FIG. 9, the sections 55, 56 around the openings 62 and 63 are also covered with wrapping 64 which is similar to the wrapping 61 covering regions 51 and 52.

Next, fourth outer regions 57 and 58 follow which are similar in structure and composition to second outer regions 53 and 54. Regions 57 and 58 narrow down into fifth outer regions 59 and 60 as illustrated in FIG. 9, which can be used, e.g. for threading the ligament prosthesis 70. All sections of prosthesis 70, including the various wrappings 61 and 64, can be fabricated together on a conventional known loom. Prosthesis 70 is especially suitable as a replacement for an anterior cruciate ligament.

Figure 10:
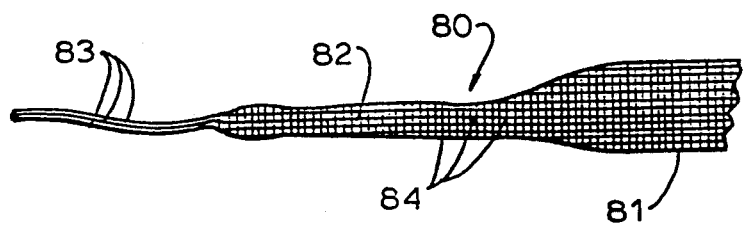
FIG. 10 represents a section of a tubular braided prosthesis manufactured from composite yarn of the present invention and provided with threading means.

FIG. 10 discloses a coreless prosthetic ligament 80 that can be prepared from the composite yarn illustrated in FIGS. 1-3. The coreless prosthetic ligament is braided with a wider central section 81, and a narrower outer section from which unwoven yarns 83 extend to form a leading section to enhance threading of prosthetic ligament 80 upon implantation. Sheath yarns 84 of prosthetic ligament 80 can be woven, braided, or knitted on a conventional loom. Sheath sections 81 and 82 of ligament prostheses 80 are tubular, i.e. coreless. Prostheses 80 is also especially suitable as a replacement for an anterior cruciate ligament.

Figure 11:
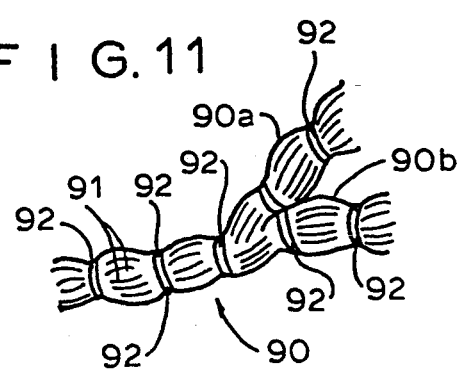
FIG. 11 represents a section of a prosthesis manufactured from composite yarn of the present invention in which the prosthesis is branched.

As illustrated in FIG. 11, a ligament prosthesis 90 can be prepared from composite yarns illustrated in Figs. 1-3 of the present invention which form a sheath about a supporting structure (not illustrated). This supporting structure can be a core formed from the composite yarns as described above, or it can be a single, integral member, formed of semi-bioabsorbable or non-bioabsorbable material forming a supporting base for yarns 91. This supporting structure, along with the bundle of yarns 91, can be divided into two branches 90a and 90b, with the yarns 91 of the prosthesis retained on the supporting structure or core at various points by fastening means 92 which can also be constituted by composite yarn of FIGS. 1-3 or by other kinds of material, e.g. totally bioabsorbable or nonabsorbable filaments. In this regard, the yarns 91 need just be bundled together without any interweaving, braiding or knitting, so long as the yarns 91 are securely held together on the core by the fastening means 92. Alternatively, yarns 92 can be woven, knitted, or braided about the core on a conventional loom to form branches 90a and 90b.

Other prosthetic structures which can be prepared with the composite yarn of the present invention are apparent to one of skill in the art in light of the disclosure herein.

It is within the scope of this invention to coat or impregnate the prosthesis with, or otherwise apply thereto, one or more materials which enhance its functionality, e.g., surgically useful substances, such as those which accelerate or beneficially modify the healing process when the prosthesis is applied to a graft site. So, for example, the prosthesis can be provided with a therapeutic agent which will be deposited at the grafted site. The therapeutic agent can be chosen for its antimicrobial properties, capability for promoting tissue repair or for specific indications such as thrombosis. Thus, for example, antimicrobial agents such as broad spectrum antibiotics (gentamicin sulphate, erythromycin or derivatized glycopeptides) which are slowly released into the tissue can be incorporated into the prosthesis to aid in combating clinical and sub-clinical infections in a surgical or trauma wound site.

To promote wound repair and/or tissue growth, one or several growth promoting factors can be introduced into the tubular prosthesis, e.g., fibroblast growth factor, platelet derived growth factor, macrophage derived growth factor, alveolar derived growth factor, monocyte derived growth factor, magainin, and so forth. To decrease abrasion, increase lubricity, etc., the prosthesis can be coated with copolymers of glycolide and lactide and polyethylene oxide, calcium salts such as calcium stearate, compounds of the Pluronic class, copolymers of caprolactone, caprolactone with PEO, polyHEMA, etc. Especially advantageous is a coating of hyaluronic acid with or without cross-linking.

Additionally, polypeptides such as Human Growth Factor (HGF) can also be coated upon or impregnated in the prosthesis to promote healing. The term "Human Growth Factor" or "HGF" embraces those materials, known in the literature, which are referred to as such and includes their biologically active, closely related derivatives. The HGFs can be derived from naturally occurring sources and are preferably produced by recombinant DNA techniques. Specifically, any of the HGFs which are mitogenically active and as such effective in stimulating, accelerating, potentiating or otherwise enhancing the wound healing process are useful herein, e.g., hEGF (urogastrone), TGF-beta, IGF, PDGD, FGF, etc. These and other useful HGFs and closely related HGF derivatives, methods by which they can be obtained and methods and compositions featuring the use of HGFs to enhance wound healing are variously disclosed, inter alia. in U.S. Pat. Nos. 3,883,497; 3,917,824; 3,948,875; 4,338,397; 4,418,691; 4,528,186, 4,621,052; 4,743,679 and 4,717,717; European Patent Applications 0 046 039; 0 128 733; 0 131 868; 0 136 490; 0 147 178; 0 150 572; 0 177 915 and 0 267 015; PCT International Applications WO 83/04030; WO 85/00369; WO 85/01284 and WO 86/02271 and UK Patent Applications GB 2 092 155 A; 2,162,851 A and GB 2 172 890 A, all of which are incorporated by reference herein. Of the known HGFs, hEGF, TGF-beta and IGF are preferred for use in the therapeutic composition of this invention.

The HGFs can be introduced with appropriate carrier such as carrier proteins disclosed, e.g., in "Carrier Protein-Based Delivery of Protein Pharmaceuticals", a paper of Biogrowth, Inc., Richmond, Calif., presented at a symposium held June 12-14, 1989 in Boston, Mass.

EXAMPLE 1

The following illustrates the manufacture of a ligament prosthesis as illustrated in FIG. 5.

A 420 denier composite yarn as illustrated in FIG. 1 was formed from a Hytrel 7246 yarn as the core component and a lactide (80 mole percent)-glycolide (20 mole percent) copolymer yarn providing the sheath component.

Six plies of the 420 denier composite yarn were wound onto 32 braider bobbins. The bobbins were loaded onto a 32 carrier braider to provide braided sheath 31. About one meter of the yarns from the 32 bobbins was pulled manually in parallel to provide a core 32 of 80,640 (420×6 ×32) overall denier. Application of braided sheath 31 also 420×6×32 or 80,640 overall denier resulted in ligament prosthesis 37 possessing an overall denier of 161,280. The stress (force in Newtons)-strain characteristics of prothesis 37 were measured and compared with the stress-strain characteristics of a human anterior cruciate ligament as reported in Noyes et al., *Journal of Bone and Joint Surgery*, Vol. 58-A, No. 8, p. 1074, et seq. (Dec. 1976). As shown in the plotted data of FIG. 6, the stress-strain characteristics of prosthesis 37 (continuous line) closely matched those of the natural tissue (broken line), an altogether remarkable achievement relative to known connective tissue prostheses.

EXAMPLE 2

The following illustrates manufacture of a tendon augmentation device 40 as illustrated in FIG. 7.

A 431 denier composite yarn as illustrated in FIG. 1 was formed from a Hytrel 7246 yarn to provide the core component 12, a lactide (80 mole percent)—glycolide (20 mole percent) copolymer yarn to provide the inner sheath component 14, and a lactide (10 mole percent)—glycolide (90 mole percent) copolymer yarn to provide the outer sheath component 16.

Six plies of the 431 denier composite yarn were wound onto 16 braider bobbins. The bobbins were loaded onto a 16 carrier braider to provide braided sections 42 and 43. About 70 mm of the yarn from the 16 braider bobbins was braided to form one of sections 42 and 43, and then the braiding was stopped. Then, about 35 mm. of the yarn from the 16 braider bobbins was pulled manually to form the unbraided center section 41, and then braiding was continued for another 70 mm of the yarn to form the other of sections 42 and 43. The resulting tendon augmentation device 40 had a total denier of 41,376 ($431 \times 6 \times 16$).

The tendon augmentation device 40 was implanted in a canine knee replacing the center third of the patellar tendon. Physical testing was carried out comparing two tendon augmentation devices 40 (TAD-1 and TAD-2) to the center third of the canine patellar tendon (⅓ P.T.) being replaced. More specifically, the stress (force in Newtons) —strain or load-deformation characteristics of devices 40 and the canine patellar tendon were measured and compared with one another.

As shown in the plotted data of FIG. 12, the responses of both tendon augmentation devices 40 (TAD 1 and TAD 2) were very similar to the one third canine patellar tendon. Moreover, tendon augmentation devices 40 (TAD 1 and TAD 2) were generally stronger than the replaced canine patellar tendon which failed when too great a load was applied thereto.

EXAMPLE 3

A composite yarn as illustrated in FIGS. 3 and 4 was fabricated using Hytrel 7246 fibers as the core component 33 and bioabsorbable sheath component fibers 35 of two different chemical compositions: first bioabsorbable fibers 35' fabricated from an 80 mole percent lactide/20 mole percent glycolide copolymer, and second bioabsorbable fibers 35" fabricated from a 10 mole percent lactide/90 mole percent glycolide copolymer. The first bioabsorbable fibers 35' were formed into yarn bundles, each yarn bundle comprising 12 filaments and having a total denier of 24. The second bioabsorbable fibers 35" were also formed into yarn bundles, each yarn bundle comprising 17 filaments and having a total denier of 27.

The composite yarn was formed using three Hytrel yarn bundles, each Hytrel yarn bundle comprising 70 filaments, to form a core component 33 of approximately 270 denier. The braided sheath component 34 was formed around the Hytrel core component 33 using an 8 carrier braider, 4 carriers each of the first and second bioabsorbable yarn bundles. The composite yarn thus formed exhibited a tensile strength of 3.19 grams/denier, and is suitable for use in fabricating a connective tissue prosthesis of the present invention.

What is claimed is:
1. A connective tissue prosthesis comprising:
   a) a core made up of a first biocompatible composite yarn extending in a lengthwise direction; and
   b) a sheath surrounding the core, said sheath being fabricated from a second biocompatible yarn;
   the first composite yarn in said core (a) comprising a non-bioabsorbable core yarn component surrounded by an at least semi-bioabsorbable sheath yarn component.
2. The connective tissue prosthesis of claim 1, wherein the second biocompatible yarn in said sheath (b) comprises a non-bioabsorbable core yarn component surrounded by an at least semi-bioabsorbable sheath yarn component.
3. The connective tissue prosthesis of claim 2 wherein the sheath yarn component is bioabsorbable.
4. The connective tissue prosthesis of claim 1 exhibiting stress-strain characteristics approximately those of the natural connective tissue replaced or augmented by the prosthesis.
5. The connective tissue prosthesis of claim 1 wherein said connective tissue prosthesis is a ligament or tendon prosthesis.
6. The connective tissue prosthesis of claim 1 wherein said connective tissue prosthesis is a human anterior cruciate ligament prosthesis.
7. The connective tissue prosthesis of claim 1 in which the core component comprises at least one filament.
8. The connective tissue prosthesis of claim 7 in which the core (a) of the prosthesis comprises multiple composite yarns.
9. The connective tissue prosthesis of claim 7 wherein the core component comprises multiple filaments.
10. The connective tissue prosthesis of claim 1 in which the sheath component comprises at least one filament.
11. The connective tissue prosthesis of claim 10 wherein the sheath yarn component comprises multiple filaments.
12. The connective tissue prosthesis of claim 1 in which the core component is manufactured from at least one polymeric material selected from the group consisting of polyethylene homopolymers, polypropylene homopolymers, ethylene-propylene copolymers, ethylene propylene terpolymers, fluorinated hydrocarbons, fluorosilicones, isobutylenes, isoprenes, polyacrylates, polybutadienes, polyurethanes, and polyether-polyester copolymers.
13. The connective tissue prosthesis of claim 1 in which the core component possesses an elongation at break of at least about 30 percent.
14. The connective tissue prosthesis of claim 1 in which the sheath component is an absorbable, relatively inelastic polymeric material derived at least in part from a monomer selected from the group consisting of glycolic acid, glycolide, lactic acid, lactide, p-dioxanone, trimethylene carbonate, e-caprolactone and hydroxycaproic acid.
15. The connective tissue prosthesis of claim 1 in which the sheath component is a lactide-glycolide copolymer.
16. The connective tissue prosthesis of claim 12 in which the sheath component is a lactide-glycolide copolymer containing from about 70 to about 90 mole percent lactide units.
17. The connective tissue prosthesis of claim 16 in which the sheath component is a lactide-glycolide copolymer containing from about 75 to about 85 mole percent lactide units.
18. The connective tissue prosthesis of claim 1 wherein the sheath (b) covering the core (a) is at least partially woven.
19. The connective tissue prosthesis of claim 18 wherein the sheath (b) is entirely woven.
20. The connective tissue prosthesis of claim 1 further comprising at least one bioactive substance.
21. The connective tissue prosthesis of claim 1, wherein said sheath component is helically wound about said core component.

22. The connective tissue prosthesis of claim 21, additionally comprising
a second sheath component helically wound about said sheath component in a different direction.

23. The connective tissue prosthesis of claim 22, in which said second sheath component is a lactide-glycolide copolymer.

24. The connective tissue prosthesis of claim 22, wherein said first and second sheath components have different ratios of absorption.

25. The connective tissue prosthesis of claim 1, wherein said sheath component is braided around said core component.

26. The connective tissue prosthesis of claim 25, wherein said sheath component comprises a plurality of bioabsorbable fibers, said fibers comprising at least two different chemical compositions.

27. The connective tissue prosthesis of claim 1, wherein said core (a) and sheath (b) together are branched at discrete locations to form gaps between branches of said prosthesis.

28. The connective tissue prosthesis of claim 27, wherein a yarn is wrapped about said sheath (b) at discrete locations to at least temporarily retain said sheath (b) about said core (a).

29. The connective tissue prosthesis of claim 28, wherein said wrapping yarn comprises a biocompatible, non-bioabsorbable core yarn component surrounded by a at least semi-bioabsorbable sheath yarn component.

30. The connective tissue prosthesis of claim 29 wherein said sheath component of said wrapping yarn is bioabsorbable.

31. The connective tissue prosthesis of claim 1 wherein said sheath yarn component is bioabsorbable.

32. The connective tissue prosthesis of claim 1 wherein the sheath (b) covering the core (a) is at least partially braided.

33. The connective tissue prosthesis of claim 32 wherein the sheath (b) is entirely braided.

34. The connective tissue prosthesis of claim 1 wherein the sheath (b) covering the core (a) is at least partially knitted.

35. The connective tissue prosthesis of claim 34 wherein the sheath (b) is entirely knitted.

36. A connective tissue prosthesis comprising:
a tubular component fabricated from composite yarn, said yarn comprising a biocompatible, core yarn component surrounded by a biocompatible, at least semi-bioabsorbable sheath yarn component.

37. The connective tissue prosthesis of claim 36, comprising a center section where said yarn is unbraided and bordered by sections where said yarn is braided.

38. The connective tissue prosthesis of claim 37, additionally comprising
a helical wrap about said unbraided center section.

39. The connective tissue prosthesis of claim 38, wherein said helical wrap is fabricated from composite yarn comprising a biocompatible, non-bioabsorbable core yarn component surrounded by a biocompatible, at least semi-absorbable sheath yarn component.

40. The connective tissue prosthesis of claim 39, wherein said sheath component is bioabsorbable.

41. The connective tissue prosthesis of claim 36, additionally comprising
a threading member attached to an end thereof, said threading member comprising a composite yarn which comprises a biocompatible, non-bioabsorbable core yarn component surrounded by a biocompatible, at least semi-bioabsorbable sheath yarn component.

42. The connective tissue prosthesis of claim 41 wherein said sheath component is bioabsorbable.

43. The connective tissue prosthesis of claim 36 wherein said sheath component is bioabsorbable.

44. Method for manufacturing a connective tissue prosthesis, comprising
forming said connective tissue prosthesis from a first biocompatible composite yarn comprising a non-bioabsorbable core yarn component surrounded by an at least semibioabsorbable sheath yarn component.

45. The method of claim 44, wherein said connective tissue prosthesis comprises a core and a sheath, said core being at least partially surrounded by said sheath.

46. The method of claim 45, wherein said biocompatible composite yarn forms said core.

47. The method of claim 44, wherein said biocompatible composite yarn forms said sheath.

48. The method of claim 44, wherein the sheath is woven about the core.

49. The method of claim 48, wherein
the sheath is braided from braider bobbins loaded onto a carrier braider, and
the core is pulled through the thus-braided sheath.

50. The method of claim 48 wherein the sheath is braided about the core.

51. The method of claim 44 wherein said sheath component is bioabsorbable.

52. The method of claim 44 wherein the sheath is knitted about the core.

53. Method for manufacturing a tubular connective tissue prosthesis, comprising
forming a tubular component from composite yarn comprising a biocompatible, non-bioabsorbable core yarn component surrounded by a biocompatible, at least semi-absorbable sheath yarn component.

54. The method of claim 53 wherein the tubular component is formed by weaving.

55. The method of claim 53 wherein the tubular component is formed by braiding.

56. The method of claim 55, wherein the tubular component is braided from braider bobbins loaded onto a carrier braider.

57. The method of claim 53 wherein the tubular component is formed by knitting.

58. The method of claim 53 wherein the sheath component is bioabsorbable.

* * * * *